(12) United States Patent
Korpan et al.

(10) Patent No.: US 6,579,110 B2
(45) Date of Patent: Jun. 17, 2003

(54) CONNECTION ASSEMBLY FOR CONDUITS

(76) Inventors: Nikolai Korpan, Kaasgrabengasse 52/3/5, A-1190 Vienna (AT); Jaroslav Zharkov, A/C 376/7, 252146 Kiew (UA); Gerhard Hochwarter, Pfarrer Matz Gasse 7/20, A-1210 Vienna (AT)

( * ) Notice: Subject to any disclaimer, the term of this patent is extended or adjusted under 35 U.S.C. 154(b) by 65 days.

(21) Appl. No.: 09/959,217

(22) PCT Filed: Feb. 22, 2001

(86) PCT No.: PCT/AT01/00045

§ 371 (c)(1),
(2), (4) Date: Nov. 28, 2001

(87) PCT Pub. No.: WO01/63165

PCT Pub. Date: Aug. 30, 2001

(65) Prior Publication Data

US 2002/0160640 A1 Oct. 31, 2002

(30) Foreign Application Priority Data

Mar. 23, 2000 (AT) .................................. A 279/2000

(51) Int. Cl.[7] .............................................. H01R 13/58
(52) U.S. Cl. ............................ 439/191; 606/20; 285/24
(58) Field of Search ................................ 439/191, 190, 439/194, 199, 201, 271, 275; 285/131, 131.1, 39, 97, 107, 24, 332, 361, 428; 606/20

(56) References Cited

U.S. PATENT DOCUMENTS

| 3,845,974 | A | * | 11/1974 | Pelloux-Gervais | ........... 285/352 |
| 4,772,050 | A | | 9/1988 | Buehler et al. | |
| 4,924,679 | A | | 5/1990 | Brigham et al. | |
| 5,022,975 | A | * | 6/1991 | Gordon | ........ 204/277 |
| 5,194,012 | A | * | 3/1993 | Cairns | ........ 439/201 |
| 5,281,215 | A | * | 1/1994 | Milder | ........ 606/20 |
| 5,324,286 | A | * | 6/1994 | Fowle | ........ 606/23 |
| 5,423,807 | A | * | 6/1995 | Milder | ........ 606/20 |
| 5,722,842 | A | * | 3/1998 | Cairns | ........ 439/139 |
| 5,738,535 | A | * | 4/1998 | Cairns | ........ 439/138 |
| 6,179,001 | B1 | * | 1/2001 | Schutz | ........ 137/14.03 |
| 6,183,019 | B1 | * | 2/2001 | Owen | ........ 285/24 |
| 6,235,019 | B1 | * | 5/2001 | Lehmann et al. | ........ 606/22 |
| 6,315,461 | B1 | * | 11/2001 | Cairns | ........ 385/56 |

FOREIGN PATENT DOCUMENTS

| CH | 273781 | 6/1951 |
| DE | 953676 | 12/1956 |
| FR | 2466697 | 4/1981 |
| FR | 2341094 | 9/1997 |
| GB | 2140115 | 11/1984 |
| WO | 9815772 | 4/1998 |
| WO | 9947845 | 9/1999 |

* cited by examiner

*Primary Examiner*—P. Austin Bradley
*Assistant Examiner*—Phuongchi Nguyen
(74) *Attorney, Agent, or Firm*—Dykema Gossett PLLC

(57) ABSTRACT

The invention relates to a connection assembly for conduits (3, 4; 7, 8) which are arranged coaxially inside one another and which accommodate the supply flow and return flow of a cryogenic medium. Said assembly comprises a first and a second coupling half (1, 2) which can be connected to one another in a sealed manner, whereby an inner conduit (4; 8) in each coupling half (1, 2) ends in a first conical sealing surface (9; 10) and an external conduit (3; 7) in each coupling half (1, 2), which encompasses the inner conduit (4; 8), ends in an additional conical sealing surface (11; 12) that is positioned outside the first conical sealing surface (9; 10) in the radial direction. In order to establish an electrical connection simply and reliably, at least one electrical contact (18, 20) is provided within the additional conical sealing surface (11; 12) in each coupling half (1, 2).

9 Claims, 1 Drawing Sheet

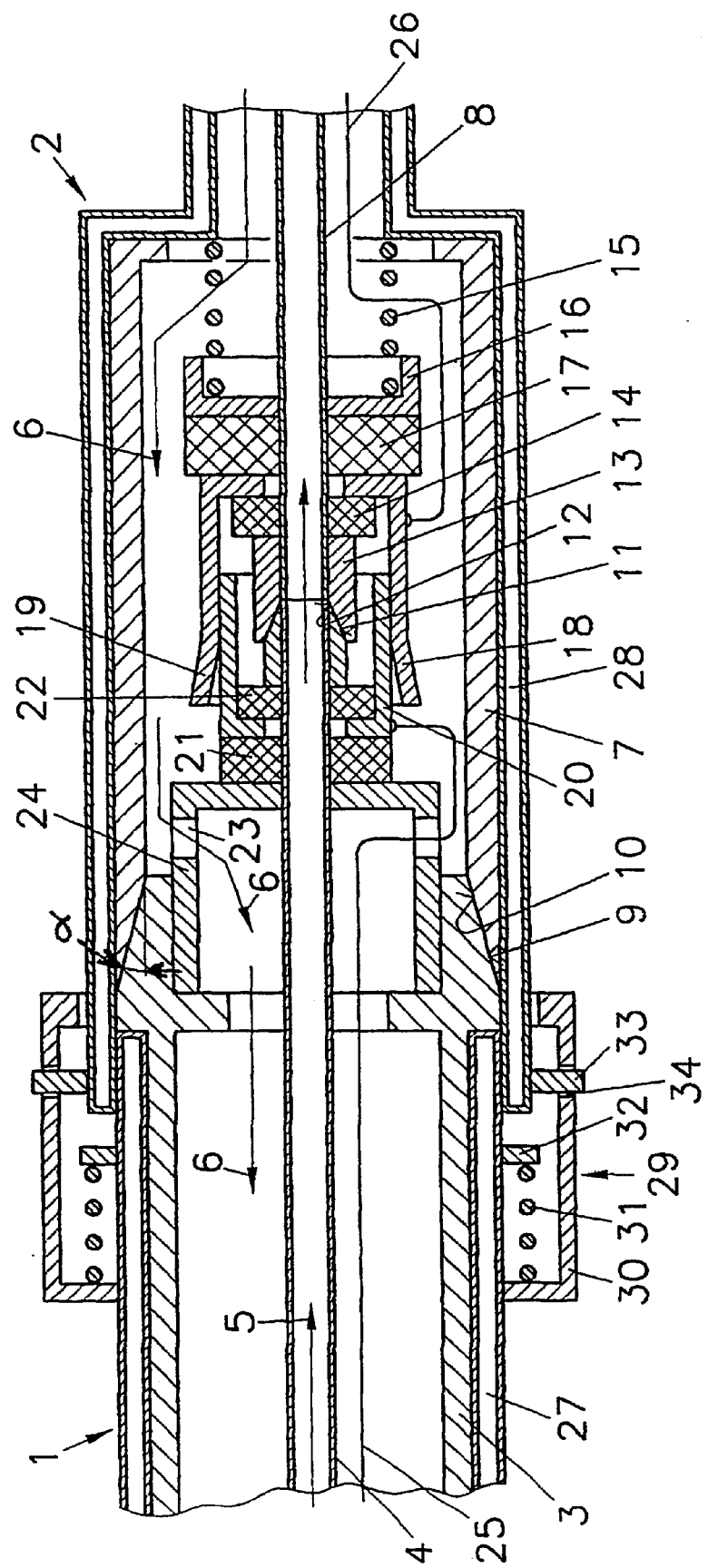

CONNECTION ASSEMBLY FOR CONDUITS

The invention relates to a connection assembly for conduits which are arranged coaxially inside one another to accommodate the supply flow and return flow of a cryogenic medium, with a first and a second coupling half which can be connected to one another in a sealed manner, whereby an inner conduit in each coupling half ends in a first conical sealing surface and an external conduit in each coupling half, which encompasses the inner conduit, ends in an additional conical sealing surface that is positioned outside the first conical sealing surface in the radial direction. Connection assemblies between the coaxial conduits for the supply flow and return flow of a cryogenic medium are needed in the medical sector in cryosurgery. A cryoapplicator is for example connected to a cryoinstrument through such a conduit, the important point thereof being that the connection be releasable. Cryosurgical instruments are utilized in the treatment of cancer as well as in general surgery, in gynecology, otorhinolaryngology, jaw surgery, orthopedics, in experimental medicine, veterinary medicine, in phytopathology and the like.

In known inventions of this type, a cryogenic medium is sealed by means of an intermediate layer such a copper for example. However, the disadvantage thereof is that such an intermediate layer may only be used a few times after which it needs to be replaced.

FR 2 466 697 A discloses a connection assembly that substantially avoids these drawbacks. However, it is often necessary to provide a separately established electrical connection between the cryoinstruments. This additional connection is complicated and makes it more difficult to handle the discrete parts. In other solutions such as those described in WO 99/47845 or U.S. Pat. No. 4,772,050 A, a potential electrical connection also needs to be established separately.

It is the object of the present invention to avoid these drawbacks and to provide, in addition to the connections of the conduits for the cryogenic medium, a simple possibility for an electrical connection.

According to the invention the solution to this object is to provide at least one electrical contact inside the additional conical sealing surface in each coupling half. The assembly in accordance with the invention protects the electrical contact and reliably isolates it from its environment.

It is particularly easy to handle since the electrical contact is automatically established as the coupling halves are connected, without the need for regarding to any particular measures.

From a constructional point of view it is particularly advantageous to have the electrical contacts coaxially arranged relative to the sealing surfaces. In this way it is not necessary to make correspond the two coupling halves in rotational direction during connection.

A particularly reliable electrical connection may be achieved by giving the electrical contacts a substantially cylindrical shape. At the low prevailing temperatures, a reliable electrical connection is achieved in this way.

A particularly advantageous hydraulic connection may be achieved by arranging the first sealing surface on a sealing member that may be displaced in axial direction and that is resiliently biased and thus connected to the inner conduit. Handling of the connection assembly is made more easy in particular when the coupling halves are connectable through a bayonet socket, and it is thereby particularly advantageous when the bayonet socket is provided with a case that is biased by a spring relative to a coupling half.

Hereinafter, the invention will be explained in more detail with the help of the variant shown in the FIGURE. The FIGURE shows an axial section through a connection assembly in accordance with the invention.

The connection assembly in accordance with the invention consists of a first coupling half 1 and of a second coupling half 2, that are shown in their connected condition. The first coupling half 1 has an external conduit 3 inside of which an inner conduit 4 is concentrically positioned. The inner conduit 4 serves for the supply flow of the cryogenic medium in the direction of the first arrow 5, whereas the external conduit 3 accommodates the return flow in direction of the second arrow 6. Analogous thereto, the second coupling half 2 has an external conduit 7 and an inner conduit 8 for the respective supply and return flow of the cryogenic medium. When the first and the second coupling half 1, 2 are connected, a conical sealing surface 9 at the end of the external conduit 3 of the first coupling half 1 and a conical sealing surface 10 at the end of the external conduit 7 of the second coupling half 2 are juxtaposed in a sealing fashion. Furthermore there is provided at the end of the inner conduit 4 of the first coupling half 1 a conical sealing surface 11 that cooperates with another conical sealing surface 12 which is provided on a sealing member 13. The sealing member 13 is carried on the inner conduit 8 of the second coupling half 2 in such a manner that it is displaceable in axial direction and is biased by a spring 15 toward the first coupling half 1. The spring 15 acts upon a spring plate 16 that communicates with an electrical contact 18 by way of an insulating disk 17. The first contact 18 is substantially shaped like a cylinder and has a widening end portion 19. Another electrical contact 20 is fastened to the first coupling half 1 by way of insulating disks 21, 22 in order to cooperate with the first contact 18 of the second coupling half 2. The return flow of the cryogenic medium occurs through bores 23 in a holding device 24 that is fastened in the external conduit 3. The electrical contacts 18, 20 are connected to instruments that have not been illustrated herein through corresponding connecting conduits 25, 26.

The external conduits 3 and 7 respectively are thermally insulated by vacuum insulations 27, 28 that are arranged outside thereof. The generatrices of the conical sealing surfaces 9, 10; 11, 12 are positioned at an angle α from 6° to 12°, here of approximately 10°, to the axis of the conduits 3, 4; 7, 8. The electrical contacts 18, 20 are configured to be press fitted, the outer diameter of one contact 18 being smaller than the inside diameter of the other contact 20 by approximately 0.3 mm. Furthermore, contact 20 has on its inner side a structure realized by four grooves that have not been illustrated and that extend over two thirds of the length.

The coupling halves 1, 2 may be connected to each other through a bayonet socket 29 that consists of a case 30 which encompasses the vacuum insulations 27, 28. The case 30 is biased by a spring 31 in a direction leading away from the second coupling half 2, the spring 31 being supported by a ring 32 that is rigidly connected to the first coupling half 1. Pins 33 that are connected to the second coupling half 2 engage with recesses 34 of case 30 in order to ensure a rigid connection. The pins 33 may also be designed as locking screws.

Thanks to the present invention it is possible not only to provide a connection for cryogenic media that is hydraulically tight and reliable but also to make certain of a reliable and durable electrical connection.

What is claimed is:

1. Connection assembly for conduits which are arranged coaxially inside one another to accommodate the supply flow and return flow of a cryogenic medium, with a first and a second coupling half which can be connected to one another in a sealed manner, whereby an inner conduit in each coupling half ends in a first conical sealing surface and whereby an external conduit in each coupling half, which encompasses the inner conduit, ends in an additional conical sealing surface that is positioned outside the first conical sealing surface in the radial direction, wherein there is provided at least one electrical contact within the additional conical sealing surface in each coupling half.

2. Connection assembly according to claim 1, wherein the electrical contacts are arranged coaxially relative to the conduits.

3. Connection assembly according to claim 1, wherein the electrical contacts are given a substantially cylindrical shape.

4. Connection assembly according to claim 1, wherein a first sealing surface is arranged on a sealing element that may be displaced in axial direction and that is resiliently biased and thus connected to the inner conduit.

5. Connector assembly according to claim 1, wherein the external conduit is thermally insulated by a vacuum insulation.

6. Connection assembly according to claim 1, wherein the conical sealing surfaces are positioned at an angle from 6° to 12° to the axis of the conduits.

7. Connector assembly according to claim 1, wherein the electrical contacts are press fitted and are preferably provided with a structured surface.

8. Connector assembly according to claim 1, wherein the coupling halves are connectable through a bayonet socket.

9. Connector assembly according to claim 8, wherein the bayonet socket is provided with a case that is biased by a spring relative to a coupling half.

* * * * *

UNITED STATES PATENT AND TRADEMARK OFFICE
CERTIFICATE OF CORRECTION

PATENT NO.   : 6,579,110 B2
DATED        : June 17, 2003
INVENTOR(S)  : Nikolai Korpan, Jaroslav Zharkov and Gerhard Hocwarter It is certified that error appears in the above-identified patent and that said Letters Patent is hereby corrected as shown below:

<u>Title page,</u>
Item [30], Foreign Application Priority Data, should read
-- Feb. 23, 2000 (AT) ………………………….. A 279/2000 --

Signed and Sealed this

Seventh Day of October, 2003

JAMES E. ROGAN
*Director of the United States Patent and Trademark Office*